United States Patent
Gill et al.

(10) Patent No.: US 12,018,316 B2
(45) Date of Patent: Jun. 25, 2024

(54) METHODS FOR ASSEMBLING NUCLEIC ACIDS

(71) Applicant: CODEX DNA, INC., San Diego, CA (US)

(72) Inventors: John E. Gill, San Marcos, CA (US); Lixia Fu, San Diego, CA (US); Daniel G. Gibson, Carlsbad, CA (US)

(73) Assignee: TELESIS BIO INC., San Diego, CA (US)

( * ) Notice: Subject to any disclaimer, the term of this patent is extended or adjusted under 35 U.S.C. 154(b) by 503 days.

(21) Appl. No.: 17/185,609

(22) Filed: Feb. 25, 2021

(65) Prior Publication Data
US 2021/0277446 A1 Sep. 9, 2021

Related U.S. Application Data (60) Provisional application No. 62/984,670, filed on Mar. 3, 2020.

(51) Int. Cl.
*C12Q 1/6806* (2018.01)
*C12P 19/34* (2006.01)
*C12Q 1/6862* (2018.01)

(52) U.S. Cl.
CPC ............ *C12Q 1/6806* (2013.01); *C12P 19/34* (2013.01); *C12Q 1/6862* (2013.01);
(Continued)

(58) Field of Classification Search
None
See application file for complete search history.

(56) References Cited

U.S. PATENT DOCUMENTS 6,472,184 B1 * 10/2002 Hegemann ....... C07K 14/43595
435/6.12
8,999,679 B2 4/2015 Che et al.
(Continued)

FOREIGN PATENT DOCUMENTS

EP 320308 B1 11/1993
WO 2018148511 A1 8/2018
(Continued)

OTHER PUBLICATIONS

Au et al. Gene Synthesis by a LCR-Based Approach: High-Level Production of Leptin-L54 Using Synthetic Gene in *Escherichia coli*. Biochemical and Biophysical Research Communications 248:200-203. (Year: 1998).*

(Continued)

*Primary Examiner* — Samuel C Woolwine
(74) *Attorney, Agent, or Firm* — Richard San Pietro

(57) ABSTRACT

The invention provides methods of assembling a DNA molecule having a desired sequence. The methods involve contacting a DNA ligase with a plurality of short oligonucleotides to be assembled and performing the ligase chain reaction to thereby generate a set of polynucleotides. Oligonucleotides in the plurality overlap with and are complementary to a sequence of at least one other oligonucleotide in the plurality, and at least 50% of the oligonucleotides in the plurality are 6-30 nucleotides in length. The set of polynucleotides produced are contacted with a DNA polymerase and dNTPs in a mixture to join the set of polynucleotides and thereby create a DNA molecule having a desired sequence by polymerase chain assembly. The method allows for production of oligonucleotides of any length having very high sequence fidelity to a desired sequence.

32 Claims, 8 Drawing Sheets

(52) U.S. Cl.
CPC . *C12Q 2521/501* (2013.01); *C12Q 2525/204* (2013.01); *C12Q 2531/113* (2013.01); *C12Y 605/00* (2013.01)

(56) References Cited

U.S. PATENT DOCUMENTS

| | | | |
|---|---|---|---|
| 10,494,671 | B2 | 12/2019 | Hendricks et al. |
| 2002/0072095 | A1 | 6/2002 | Hartley et al. |
| 2002/0168341 | A1* | 11/2002 | Graham ................ C12N 15/86 435/235.1 |
| 2003/0068643 | A1 | 4/2003 | Brennan et al. |
| 2003/0119025 | A1 | 6/2003 | Olek et al. |
| 2003/0152984 | A1* | 8/2003 | Aygun ................ C12N 15/10 435/6.16 |
| 2006/0134628 | A1 | 6/2006 | Evans |
| 2007/0009928 | A1 | 1/2007 | Lathrop et al. |
| 2008/0044862 | A1 | 2/2008 | Schatz et al. |
| 2008/0300842 | A1 | 12/2008 | Govindarajan et al. |
| 2009/0087840 | A1 | 4/2009 | Baynes et al. |
| 2010/0047876 | A1 | 2/2010 | Church |
| 2010/0173364 | A1 | 7/2010 | Evans, Jr. et al. |
| 2012/0156731 | A1 | 6/2012 | Huang et al. |
| 2013/0059761 | A1 | 3/2013 | Jacobson et al. |
| 2014/0038240 | A1 | 2/2014 | Temme et al. |
| 2015/0010953 | A1 | 1/2015 | Lindstrom et al. |
| 2016/0186166 | A1 | 6/2016 | Poehmerer et al. |
| 2016/0215316 | A1 | 7/2016 | Pedersen et al. |
| 2016/0340670 | A1 | 11/2016 | Lou et al. |
| 2016/0378913 | A1 | 12/2016 | Hillson |
| 2018/0105806 | A1 | 4/2018 | Voigt et al. |
| 2018/0148511 | A9 | 5/2018 | Bernett et al. |
| 2018/0153835 | A1 | 6/2018 | Shinde et al. |
| 2018/0291413 | A1 | 10/2018 | Chiocchini et al. |
| 2018/0320166 | A1 | 11/2018 | Lajoie et al. |
| 2019/0256843 | A1* | 8/2019 | Rinehart ............ C12N 15/1093 |

FOREIGN PATENT DOCUMENTS

| | | |
|---|---|---|
| WO | 20180154384 A1 | 8/2018 |
| WO | WO 2020/001783 | 1/2020 |

OTHER PUBLICATIONS

Dunn et al. Ligation of Hexamers on Hexamer Templates to Produce Primers for Cycle Sequencing or the Polymerase Chain Reaction. Analytical Biochemistry 228:91-100. (Year: 1995).*
Chalmers et al. Scaling Up the Ligase Chain Reaction-Based Approach to Gene Synthesis. BioTechniques 30:249-252. (Year: 2001).*
Zhou et al. Microfluidic PicoArray synthesis of oligodeoxynucleotides and simultaneous assembling of multiple DNA sequences. Nucleic Acids Research 32:5409-5417. (Year: 2004).*
Stemmer et al. Single-step assembly of a gene and entire plasmid from large numbers of oligodeoxyribonucleotides. Gene 164:49-53. (Year: 1995).*
Pachuk et al. Chain reaction cloning: a one-step method for directional ligation of multiple DNA fragments. Gene 243:19-25. (Year: 2000).*
Roth et al. A Rapid and Simple Method for DNA Engineering Using Cycled Ligation Assembly. PLoS One 9(9):e107329. (Year: 2014).*
de Kok, Stephan et al., ACS Synthetic Biology, pubs.acs.org/synthbio, Dec. 2013, pp. A-J.
Engler, Carola et al., PLos one, vol. 3, (11), e3647, Nov. 2008.
Weber, Ernst et al., PLos one, vol. 6, (5), e19722, May 2011.
Barany, Francis, "The Ligase Chain Reaction in a PCR World," PCR Methods and Applications, Cold Spring Harbor Laboratory Press, pp. 5-149, 1991.
Tian, Jingdong et al., "Accurate multiplex gene synthesis from programmable DNA microchip," Letters to Nature, vol. 432, Dec. 23/30, 2004, pp. 1050-1054.
Zhang, Shasha et al., J. of Biol. Eng., (2015), 9:23 , pp. 1-10.
PCT International Search Report and Written Opinion in International Application No. PCT/US2021/019656, dated May 7, 2021, 9 pages.

* cited by examiner

METHODS FOR ASSEMBLING NUCLEIC ACIDS

CROSS-REFERENCE TO RELATED APPLICATION

This application claims the benefit under 35 USC § 119(e) to U.S. Application Ser. No. 62/984,670 filed Mar. 3, 2020, the entire contents of which is incorporated herein by reference in its entirety.

FIELD OF THE INVENTION

The invention pertains to methods of synthesizing and constructing nucleic acids with low error rates.

BACKGROUND OF THE INVENTION

The assembly of DNA is a critical technology for synthetic biology and genetic engineering that has attracted enormous efforts directed towards improving the efficiency, fidelity, and simplicity of DNA assembly methods. Various methods of DNA assembly are known and have particular advantages. The Gibson Assembly method utilizes the complementarity of DNA sequences (Gibson et al., 2009) while Golden Gate Assembly is based on restriction digestion and ligation methods. One important aspect of DNA synthesis is the importance of achieving and maintaining sequence fidelity in the DNA sequence, i.e. to produce a DNA molecule having a very low error rate. Chemical synthesis of starting oligonucleotides inputs error into synthesized sequences, which are then propagated as the desired DNA molecule is assembled and amplified.

The goal of increasing the fidelity of DNA synthesis and assembly has been addressed through the use of error correction enzymes to reduce errors in synthetic DNA constructed from synthetic oligonucleotides. While the use of error correction enzymes has been an important development, their use also has disadvantages. Furthermore, current methods often rely on synthesizing a desired DNA molecule on a DNA chip or other solid phase device, rendering the method substantially less suitable for automated synthesis. These methods are also time consuming and are less efficient in DNA synthesis. New methods of assembling DNA molecules produced from synthetic oligonucleotides and having very high sequence fidelity and that do not require the use of error correction enzymes are still needed.

SUMMARY OF THE INVENTION

The invention provides methods of assembling a DNA molecule having a desired sequence. The methods involve contacting a DNA ligase with a plurality of short oligonucleotides to be assembled and performing the ligase chain reaction to thereby generate a set of polynucleotides. Oligonucleotides in the plurality overlap with and are complementary to a sequence of at least one other oligonucleotide in the plurality, and at least 50% of the oligonucleotides in the plurality are 8-22 nucleotides in length. The set of polynucleotides are optionally contacted with a DNA polymerase and dNTPs in a mixture to join the set of polynucleotides and thereby create a DNA molecule having a desired sequence by polymerase chain assembly. The DNA fragments can be optionally assembled using the polymerase chain assembly reaction, or another oligonucleotide assembly reaction (e.g. OSOS), and optionally amplified through PCR.

In a first aspect the invention provides methods of assembling a DNA molecule having a desired sequence. The methods involve contacting a DNA ligase with a plurality of short oligonucleotides having at least a portion of the desired sequence of the DNA molecule to be assembled to create a mixture. At least a portion of the short oligonucleotides in the plurality overlap with and are complementary to a portion of the sequence of at least one other short oligonucleotide in the plurality, and at least two of the short oligos abut one another when bound to their complementary sequence(s). At least 50% of the short oligonucleotides in the plurality can be 8-30 nucleotides in length. The methods also involve performing a ligase chain reaction on the mixture to thereby generate a set of polynucleotides, and contacting the set of polynucleotides with a DNA polymerase and dNTPs to join the set of polynucleotides, and to thereby assemble the DNA molecule having the desired sequence.

In one embodiment the set of polynucleotides is joined by polymerase cycling assembly and/or by a DNA assembly reaction (e.g. an OSOS reaction). In one embodiment the method involves contacting the plurality of short oligonucleotides with a kinase before or simultaneous with the contacting of the short oligonucleotides with the DNA ligase. In one embodiment the DNA ligase is a thermostable DNA ligase, for example Taq ligase. The abutting short oligos can have a phosphorylated 5' terminal nucleotide of a first short oligo and a 3' hydroxyl on a 3' terminal nucleotide of a second short oligo. The method can include amplifying the DNA molecule having the desired sequence using the polymerase chain reaction. In one embodiment the method is performed in solution. In various embodiments the DNA molecule having the desired sequence can be 100-10,000 base pairs or 100-5,000 base pairs in length. In one embodiment the desired sequence further comprises a universal 5' flanking sequence and a universal 3' flanking sequence. The methods can also involve combining multiple pools of the sets of polynucleotides to join the polynucleotides via PCA (Polymerase Cycling Assembly).

In one embodiment at least 10 cycles of the polymerase chain reaction can be done to amplify the DNA molecule having the desired sequence. In various embodiments the plurality of short oligonucleotides can contain at least 10 short oligonucleotides, or at least 20 short oligonucleotides, or from 2 to 250 short oligonucleotides. In one embodiment the plurality of short oligonucleotides are 10-18 nucleotides in length. At least 50% of the short oligonucleotides in the plurality can be 10-18 nucleotides in length. In another embodiment at least 75% of the oligonucleotides in the plurality are 6-18 or 10-18 or 16-18 nucleotides in length at the start of the method. The method can be performed without the use of restriction enzymes. The assembled DNA molecule of desired sequence produced by the methods can have an error rate of fewer than 1 error per 2000 base pairs, or fewer than 1 error per 14000 base pairs. The error rates can be obtained in the method without the use of error correction enzymes.

In some embodiments the plurality of short oligonucleotides are comprised in at least 15 pools of oligonucleotides. The method can be done entirely in vitro. In some embodiments the oligonucleotides can be 8-mers or 16mers. The DNA molecule can be assembled in the method can be scarless, i.e. can be assembled with scarless assembly. In one embodiment the plurality of short oligonucleotides comprises more than 64 short oligonucleotides. The method can be conducted without the use of linker, adaptor, or spacer DNA molecules. In the method the ligase chain reaction can have at least 5 cycles of denaturation, annealing, and ligation. In any embodiment the plurality of short oligonucleotides can have more than 64 short oligonucleotides. And in various embodiments less than 10% or less than 1% of the oligonucleotides in the mixture are longer than 20 or longer than 30 nucleotides in length.

DESCRIPTION OF THE DRAWINGS

FIG. 1 is a general illustration of one embodiment of the invention. Aspects of the methods are shown including single-stranded oligonucleotides, annealing, ligation, and abutting oligos joined by a ligase in the method. Optional further assembly and/or amplification is also depicted.

FIGS. 4A-4B.

DETAILED DESCRIPTION OF THE INVENTION

The present invention provides methods of assembling a DNA molecule having a desired sequence. The methods involve contacting a DNA ligase with a plurality of short oligonucleotides comprising at least a portion of the DNA molecule to be assembled to thereby generate a set of polynucleotides or DNA fragments in a mixture. At least a portion of the oligonucleotides in the plurality overlap with and are complementary to a sequence of at least one other oligonucleotide in the plurality, and at least 50% of the oligonucleotides in the plurality can be 8-22 nucleotides in length. The mixture formed can be contacted with a DNA polymerase and dNTPs and, optionally, subjected to a DNA assembly reaction (e.g. OSOS or PCA) to join the set of DNA fragments and thereby create a DNA molecule having a desired sequence by polymerase chain assembly. The methods can therefore be applied in a hierarchical DNA assembly method. The plurality of oligonucleotides can be joined using the ligase chain reaction, and DNA fragments can be assembled using polymerase cycling assembly (PCA) and/or OSOS assembly, and optionally amplified using PCR or another DNA amplification procedure.

The synthesis of polynucleotides and DNA fragments has focused on using longer oligonucleotides in synthesis in order to maximize the ability to form larger pieces of DNA and thereby optimize synthesis. It has been believed that longer oligonucleotides are beneficial in because of their greater ability to span repetitive regions and provide greater specificity in assembly reactions due to higher melting temperatures (Tm) in PCR and other DNA assembly or amplification reactions. The oligonucleotides or DNA fragments produced by these processes have then been subjected to error correction using error correction enzymes (e.g. mismatch endonucleases) to remove errors and increase the accuracy of the desired DNA sequence. After error correction the DNA fragments can then be assembled and/or amplified using DNA amplification procedures.

While it has been thought that the ligase chain reaction (LCR) requires longer oligonucleotides to provide ample opportunities for annealing oligonucleotides in solution, the present inventors discovered unexpectedly that when the ligase chain reaction is performed on short oligonucleotides as disclosed herein, a greater sequence fidelity in the product DNA sequence is obtained. The increase in sequence fidelity is so substantial that it surprisingly eliminates the need to perform an error correction step, e.g. a step using error correction enzymes to correct mismatched nucleotide pairs and achieve higher sequence fidelity. The present inventors also discovered that the described benefits can be obtained when the ligase chain reaction is performed on short oligonucleotides in solution. In any embodiment the methods can be conducted without the use of any kind of restriction enzyme (e.g. a restriction endonuclease). In any embodiment the methods can be conducted entirely in vitro, i.e. without the use of cloning or the need to clone nucleic acids in live organisms. In any embodiment the methods can be conducted in solution, i.e. without having any of the oligonucleotides (or any part of a forming polynucleotide) or reaction components in the method (or any step thereof) bound to or immobilized on a DNA chip, bead, surface, or other solid phase. In some embodiments therefore the entire formed oligonucleotide or DNA fragment is in solution, i.e. not even a starting oligonucleotide or seed oligonucleotide (e.g. representing the end of a polynucleotide chain) is bound to a solid support, at any point in the method. The methods are therefore highly suitable for automated synthesis and provide high yields of high fidelity product DNA. Any of the embodiments can be conducted so that no component of the reaction is immobilized on a solid phase.

Ligation refers to covalently attaching polynucleotide sequences in a covalent bond to form a single sequence. A ligase can catalyze the formation of a covalent phosphodiester bond between a 5'-P end of a first oligo and a 3'-OH end of a second oligo. Either or both of the first and second oligos can be annealed to a complementary strand and nucleotides bearing the 5'-P and 3'-OH can be adjacent to one another when acted upon by the ligase. In other embodiments ligation can also encompass other means of covalently attaching the oligos, for example using chemical means. The term oligo is used herein to denote an oligonucleotide.

The Methods

The methods generally involve providing one or more pools containing a plurality of short oligonucleotides of any length described herein. In some embodiments the short oligonucleotides can be treated with a kinase to add a 5' phosphate group, but a 5' phosphate group can also be added during chemical oligo synthesis or simultaneously with a synthesis reaction (e.g. LCR). The short oligonucleotides can therefore be contacted with a kinase before or simultaneous with the contacting of the short oligonucleotides with the DNA ligase, or before or after LCR. In some embodiments the reaction can optionally be conducted on a thermocycler to ligate the initial or short oligos together, thus forming larger oligos or DNA fragments. In one embodiment this can be done by subjecting the plurality of short oligonucleotides to the ligase cycling reaction (LCR). The resulting DNA fragments (or larger oligos) can then be subjected to further assembly and/or amplification reactions to build larger DNA molecules or amplify their quantity. The term polynucleotide refers to a polymer composed of nucleotide units. The term oligonucleotide refers to a polynucleotide having up to 30 nucleotides. A DNA fragment refers to a polynucleotide having more than 30 nucleotides.

The short oligos can be provided in pools or sets for synthesis into DNA fragments or longer oligonucleotides. In any embodiment the short oligos can be synthesized using chemical synthesis methods. A set comprises all of the oligos that will be joined into a longer oligonucleotide molecule, which may then be further combined to make a larger DNA fragment or oligonucleotide. A set can be comprised in a single pool having overlapping oligos, or can be comprised in more than one pool that will be combined in the method to form a longer oligonucleotide. The short oligos in one or more pools can comprise a set, and oligos in a set can overlap with and be complementary to (in terms of Watson-Crick base pairing) at least a portion of at least one other oligo in the set, or to two oligos in the pool or set, or to more than two oligos in the pool or set. In one embodiment the oligos can be provided in multiple sets, where each set is comprised in two pools. In different embodiments oligos can be assembled in a single pool or by combining two pools. The two pools can be combined and subjected to LCR, and optionally to PCA and/or OSOS and/or PCR, and longer oligonucleotides or DNA fragments thereby produced. One or more pools of oligos or DNA fragments can then also be subjected to LCR, and optionally OSOS and/or PCA and/or PCR. A hierarchal assembly can therefore be performed to arrive at the product DNA molecule having a defined and desired sequence. The defined and desired sequence can be a particular and pre-defined sequence decided prior to beginning the methods, and the short oligonucleotides can be designed to produce the particular defined and desired sequence in the methods.

The short oligos together can comprise at least a portion of the sequence of the DNA molecule to be assembled and having a desired sequence. The method can be performed using as many pools as desirable. In various embodiments one pool, or two pools, or more than 2 pools, or more than 4 pools, or more than 8 pools, or more than 20 pools or more than 25 pools of short oligos of the size described herein can be utilized. In various embodiments the pools can contain at least 8 short oligos, or at least 16 short oligos, or at least 32 short oligos, or at least 64 short oligos or 8-32 short oligos or 8-64 short oligos. In various embodiments polyethylene glycol or glycerol or betaine or sorbitol, or a combination of any of them, can be added to the mixture subjected to LCR, or to the mixture subjected to PCA and/or OSOS and/or PCR to assemble the DNA molecule of the desired sequence.

The method of the invention can assemble the DNA molecule having the desired sequence as a scarless DNA molecule. By scarless DNA is mean DNA that does not have any nucleotide(s) introduced by or from the process of synthesizing the DNA (e.g. residue nucleotides from a linker molecule), or the product DNA does not have any nucleotides present that were not present in one of the original short oligonucleotides, for example the product DNA does not have any such nucleotides present at the junction where two oligonucleotides are joined. The scarless DNA molecule of desired sequence can correspond to a natural sequence, a synthetic sequence, or can be an engineered sequence. The methods can also join short oligonucleotides in a reaction where all of the short oligonucleotides are present in solution, i.e. in some embodiments none of the oligonucleotides being combined is present on or attached to a solid phase (e.g. a DNA chip, bead, or microarray). In some embodiments the ligase chain reaction is performed on the oligonucleotides where all oligonucleotides in the reaction are present in solution; or wherein neither of any two oligos that anneal are present on or attached to a solid phase or solid support. The methods can also assemble the oligos or DNA fragments and/or DNA molecule of desired sequence simultaneously, i.e. wherein a single reaction assembles the oligonucleotides into a longer oligo or DNA fragment. Simultaneous assembly is therefore distinguished from methods where the oligonucleotides are assembled sequentially, i.e. where a second oligo is annealed to a first oligo, and then a third oligo is annealed to the second oligo, and so on, as oligos are added to the end of a growing duplex or chain in sequential order. In a simultaneous reaction all of the oligos that will form the longer oligo or DNA fragment, or the product DNA molecule, are present in the solution at the same time. And a plurality of oligos (or all oligos) present simultaneously in the solution participate in the reaction, anneal and are joined by the ligase. A simultaneous reaction can also be a one-step reaction. In any embodiment the methods can be conducted and the DNA molecule synthesized without the use of a restriction enzyme or restriction endonuclease. In any embodiment the DNA molecule of desired sequence is not a circular DNA. In any embodiment the DNA molecule of desired sequence is, optionally, not a vector DNA.

In any embodiment the methods do not use linker or spacer sequences or oligos. Linker or adaptor DNA or sequences can be short oligonucleotides that can be ligated to the ends of other DNA or oligonucleotide molecules. Linker, adaptor, or spacer molecules or sequences can also be used to provide for release of a polynucleotide from a solid support, or to link or tether a polynucleotide to a solid support. These molecules or sequences can provide sticky ends and/or overhangs allowing for ligation. Linker, adaptor, or spacer DNA sequences can also comprise, for example, restriction sites, recognition sites (e.g for a nicking endonuclease), poly-U sequences, or can be a sequence having one or more uracil residues. Linkers, adaptors, or spacer DNA or sequences are any nucleotide or nucleotide sequence not found in the DNA molecule of desired sequence assembled in the methods. In any embodiment of the methods none of the oligonucleotides used in the method comprises a linker, adaptor, or spacer sequence. In any embodiment the method does not involve the use of linkers, adaptors, or spacer DNA or sequences. This is a further advantage of the methods and makes the methods more suitable for automation.

The DNA molecule assembled by the methods and having a desired sequence can be any DNA molecule. In various embodiments the DNA molecule having a desired sequence is from 100-5,000 bp in length, or from 100-10,000 bp in length, or from 5,000-10,000 bp in length, or from 5,000-15,000 bp in length, or from 10,000-15,000 bp in length, or from 10,000-20,000 bp in length, or from 10,000-25,000 bp in length, or more than 1 kb or more than 2 kb or more than 3 kb or more than 5 kb in length, or more than 10 kb in length, or more than 15 kb in length, or more than 20 kb in length.

Error Rate

The methods of the invention can produce a DNA molecule of desired sequence that has an error rate of less than 1 error per 2,000 base pairs, or less than 1 error per 5,000 base pairs, or less than 1 error per 7,500 bps, or less than 1 error per 10,000 bps, or less than 1 error per 11,000 bps, or less than 1 error per 12,000 bps, or less than 1 error per 13,000 bps, or less than 1 error per 14,000 bps, or less than 1 error per 15,000 bps, or less than 1 error per 16,000 bps or less than 1 error per 17,000 bps, or less than 1 error per 20,000 bps, or less than 1 error per 25,000 bps. In any embodiment the method allows for the production of a DNA molecule having the very low error rates described herein without the use of any error correction enzymes. Error correction enzymes are enzymes utilized to correct errors in DNA synthesis. In one embodiment error correction enzymes can identify a mismatch in a duplex DNA molecule, and can initiate a double-stranded cut as a result of the mismatch. The double-stranded cut can be at or near the site of the mismatch. The mismatch can be excised by the same or other enzymes (e.g. an exonuclease) and the DNA re-assembled without the sequence error and in the correct sequence. One example of error correction enzymes are mismatch endonucleases (e.g. CEL I and/or CEL II), known to persons of ordinary skill in the art. Other (non-limiting) examples of error correction enzymes include any one or more of mung bean endonuclease, T7 endonuclease I, and endonuclease V.

Oligos

In various embodiments of the methods a DNA ligase is contacted with a plurality of short oligonucleotides having at least a portion of the desired sequence of the DNA molecule to form a mixture. The plurality of initial or short oligos used in the methods can be from 2-250 or 2-100 or 6-30 nucleotides (nt) in length, but can also be from 6-10 nt or from 6-12 nt or from 6-13 nt or from 6-14 nt or from 6-15 nt or from 6-17 nt or from 6-18 nt or from 6-19 nt or from 6-20 nt or from 6-22 nt or from 6-25 nt or from 6-30 nt or from 6-35 nt or from 5-16 nt or from 5-17 nt or from 5-18 nt or from 5-19 nt or from 7-10 nt or from 7-12 nt or from 7-15 nt or from 7-17 nt or from 7-18 nt or from 7-19 nt or from 7-20 nt or from 7-25 nt or from 7-30 nt or from 7-35 nt or from 8-12 nt or from 8-15 nt or from 8-17 nt or from 8-18 nt or from 8-19 nt or from 8-20 nt or from 8-21 nt, or from 8-22 nt, or from 8-25 nt or from 8-30 nt or from 8-35 nt or from 10-22 nt, or from 16-18 nt, or from 15-19 nt, or from 14-20 nt, or less than 18 nt or less than 17 nt or less than 16 nt or less than 15 nt or less than 12 nt in length. The initial or short oligos can be comprised in the one or more oligo pools. In various embodiments at least 25% or at least 30% or at least 40% or at least 50% or at least 60% or at least 70% or at least 80% or at least 90% or at least 95% or at least 97% of the initial or short oligos in each oligo pool or set (or in the mixture in contact with the DNA ligase) can be within any of the size ranges described herein. In any embodiment the oligos in the pools or in contact with the DNA ligase can be overlapping, for example by 3 nt or by 4 nt or by 5 nt or by 6 nt or by 7 nt or by 8 nt or by 9 nt or by 10 nt or by more than 10 nt, or by about one-half the length of the oligo, which can be rounded up or rounded down or, optionally, within 1, 2, or 3 nt of the one-half length. Thus, in some embodiments the oligos are 8mers and have a 4 nt overlap with an at least partially complementary 8mer, or the oligos are 16mers and have an overlap of 8 nt with an at least partially complementary oligonucleotide. In other embodiments the short oligos in the plurality of short oligonucleotides overlap by at least 3 nt or at least 4 nt or at least 5 nt or at least 6 nt or at least 7 nt or at least 8 nt or at least 9 nt. In another embodiment the short oligos in the plurality can overlap by about one-half the length of the shorter of the overlapping oligos; for example 16mers can overlap by 8 nt. When short oligos of different lengths are used they can overlap by one-half the length of the shorter of the overlapping oligos. In any embodiment less than 10% or less than 5% or less than 3% or less than 1% of the short oligos in the mixture of DNA ligase and initial or short oligos (or in the pools for performing the ligase chain reaction) are longer than 30 nt or 29 nt or 25 nt or 22 nt or 20 nt or 18 nt or 17 nt or 16 nt.

In some embodiments a mixture of sizes can be used. In various embodiments the oligos in each pool can be of any of the length ranges described present in any of the percentage amounts described. In any embodiment the oligos, short or long, can be 5' phosphorylated. 5' phosphorylation can also be accomplished by contacting the oligos with a suitable kinase which can be done before the ligase chain reaction step. The oligos can also be pre-synthesized with a 5'-P. But any method of providing 5' phosphorylated oligonucleotides can be used. In one embodiment the kinase can be T4 polynucleotide kinase (T4PNK), but any appropriate kinase can be used.

In any embodiment of the methods or DNA assembly reactions there can be present in the mixture of DNA ligase and the plurality of short oligonucleotides no nucleic acids having a length of longer than 16 nt, or longer than 22 nt, or longer than 25 nt, or longer than 30 nt; or where less than 10% or less than 5% or less than 3% or less than 1% (by molar amount or number of oligos) of the oligonucleotides in the mixture have a length of longer than 22 nt or 25 nt or 30 nt.

In various embodiments the method can utilize oligos in one or more pools. In various embodiments a pool or set can contain 2-250 or 2-150 or 2-125 short oligos, which can be combined in the oligo pool or pair of pools. In other embodiments from 8-250 or from 8-150 or from 8-125 short oligos can be comprised in a pool or set and used to initiate the method. In more embodiments the plurality of short oligos can comprise one or more pool size(s) or set sizes of at least 15 oligos or at least 20 oligos or at least 50 oligos, or more than 64 oligos, or more than 65 oligos, or at least 75 oligos, or at least 100 oligos or 15-250 oligos or 20-250 oligos or 30-250 oligos or 40-250 oligos or 50-250 oligos or 20-200 oligos or 30-200 oligos or 40-200 oligos or 50-200 oligos or 15-150 oligos or 20-150 oligos or 30-150 oligos or 40-150 oligos or 50-150 oligos.

In the methods the oligonucleotides can be present together to form a mixture. The mixture can contain oligos in a suitable buffer and oligos can anneal to complementary oligos in the mixture. In some embodiments the overlap is about one-half the length of the oligo. Thus, a 16 nt oligo can overlap with another oligo in the mixture by 8 nt. In other embodiments the overlap can be more or less than one-half the length of the oligo, for example the overlap can be one-half the length of the oligo plus or minus 1 or 2 or 3 or 4 or 5 nt.

The plurality of short oligos (or set of DNA fragments), when mapped out and placed next to each other, can comprise at least a portion of the sequence (or the entire sequence) of the product DNA molecule being assembled and having the desired sequence. In some embodiments at least a portion of the short oligonucleotides overlap with and are complementary to a portion of the sequence of at least one other short oligonucleotide in the plurality. The plurality of oligos can be divided into one or more pools to comprise an oligo set. In some embodiments the short oligonucleotides in the plurality overlap with two other short oligonucleotides in the plurality except for the end (short) oligonucleotides, which can overlap with only one other short oligonucleotide. The end short oligonucleotides are those will comprise the 5' and 3' end of the product nucleic acid molecule being assembled (or that will comprise the 5' and 3' end of flanking sequences, if present). Optionally, the end short oligos are not part of any flanking sequence.

Figure 1:
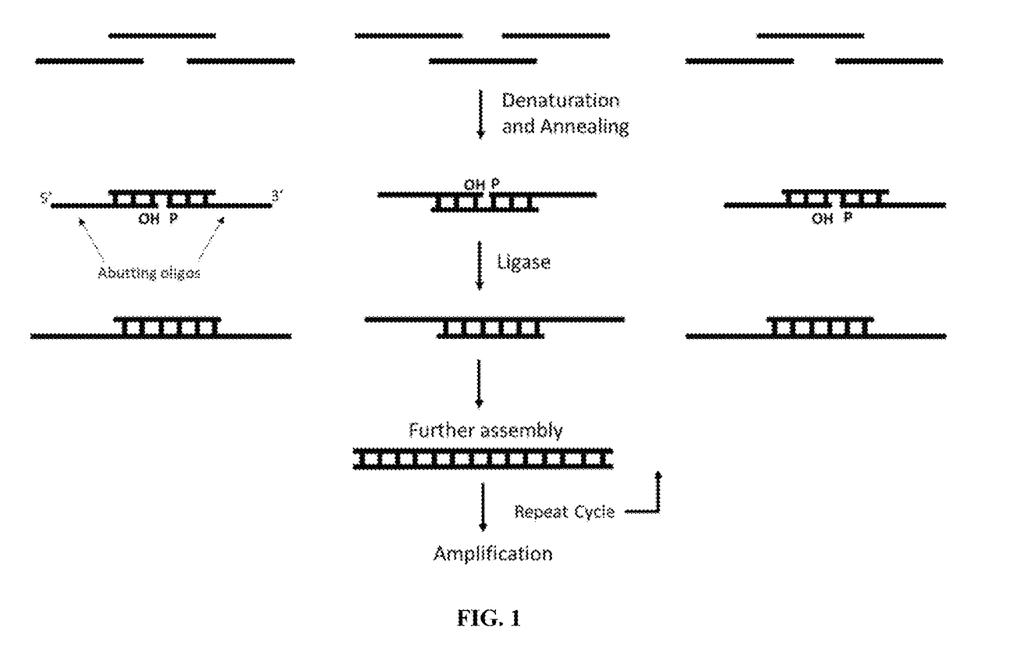

While short oligos can be of any length recited herein, in various embodiments at least 50% or at least 60% or at least 70% or at least 80% or at least 90% of the short oligonucleotides overlap with two other short oligonucleotides. At least two of the short oligonucleotides abut one another when bound to their complementary sequence, as depicted in FIG. 1—abutting oligos are bound to a complementary sequence and the 5' nucleotide of a first oligo is bound to a nucleotide on the complementary sequence that is adjacent to the nucleotide that is bound to the 3' nucleotide of a second oligo, or vice versa, i.e. the first and second oligos are abutting or adjacent to one another. In any embodiment binding can refer to Watson-Crick base pairing or by hydrogen bonds between base pairs. Where short oligonucleotides are annealed to a complementary sequence and abut one another they can be covalently ligated by a DNA ligase. The 5'-P of the first oligo can be ligated to the 3'-OH of the second oligo by the ligase. In some embodiments the overlap comprises about one-half the length of the oligo being joined to an adjacent oligo (e.g. a 16mer can have an 8 bp overlap with one or two adjacent oligos). In some embodiments at least 75% or at least 80% or at least 90% of the short oligonucleotides can bind to a complementary oligo sequence in the mixture and two out of the three oligonucleotides will abut one another when so bound.

In some embodiments a DNA ligase can be contacted with the plurality of initial or short oligos (or with a set of DNA fragments) to create a mixture. Examples of DNA ligases that can be used include T4 DNA ligase (from bacteriophage T4), but any suitable DNA ligase can be used that catalyzes the formation of a covalent phosphodiester bond between the 3' hydroxyl end of one annealed oligonucleotide and the 5' phosphate end of a directly adjacent annealed oligo, thereby joining oligonucleotides to produce a covalent bond and a longer oligonucleotide or double-stranded DNA fragment. Additional examples of DNA ligases include (but are not limited to) T3 DNA ligase, T7 DNA ligase, Taq DNA ligase, and 9° N™ DNA ligase. In some embodiments the DNA ligase can be a thermostable DNA ligase, i.e. stable at a temperature greater than 70° C.; but in other embodiments a thermostable ligase can be stable at a temperature greater than ° 90 C or greater than 93° C. or greater than 94° C. or from 90-100° C., and for any period of time selected from at least 30 second or at least 60 seconds or 30-60 second to at least 30 minutes to at least 60 minutes). The thermostable DNA ligase can also remain active after exposure to a temperature of at least 70° C., or at 85° C. for 20 minutes or 30 minutes or 1 hour. In various embodiments the contacting can include ATP and/or NAD, or other cofactors or requirements for the specific ligase being used.

The DNA molecule of desired sequence can be of any sequence. In any embodiment the methods can be sequence independent, meaning that there is no particular required sequence that must be present for the methods to function and produce the DNA molecule of desired sequence. In various embodiments the DNA molecule of desired sequence synthesized in the methods can be at least 20 bp or at least 30 bp or at least 40 bp or at least 60 bp or 40-60 bp or 20-100 bp. Since the method can apply hierarchal assembly a DNA molecule of desired sequence of any size can be assembled in the methods, for example one of greater than 1 kb or 1-3 kb or greater than 10 kb or 1-10 kb or 1-12 kb. The DNA molecule of desired sequence can also comprise flanking sequences, for example UTRs, promoters, introns, or flanking homology sequences. In various embodiments the DNA molecule of desired sequence can have a GC content of at least 30% or at least 40% or at least 50% or at least 60% or 30-60%.

Ligase Chain Reaction

The ligase chain reaction (LCR) (also called the ligase cycling reaction) is a method of DNA assembly, and can optionally be paired with subsequent polynucleotide assembly reaction (e.g. PCA, OSOS, or overlap extension PCR (OE-PCR) and amplification of the DNA product (e.g. by PCR). LCR involves steps of denaturation, annealing, and ligation by ligase of abutting oligonucleotides in the steps of the reaction, which can be cycled and thus repeated. In LCR a DNA ligase is contacted with first and second abutting oligos that are annealed to a third oligo having a sequence that is complementary to and overlaps a portion of at least one (or both) of the first and second oligonucleotides (FIG. 1). The nucleotide at the 5' terminal end of the first oligo can be ligated by the DNA ligase to the nucleotide at the 3' end of the second oligo. The nucleotide at the 5' end of first oligo can be phosphorylated, and the nucleotide at the 3' end of the second oligo can have a 3'-OH, to thereby provide the 5'-P and 3'-OH substrates for the ligase on the abutting first and second oligos. The ligated oligos (now a longer oligonucleotide) and the (complementary) third oligo can now be denatured and the cycle can be repeated. In various embodiments at least 2 or at least 5 or at least 10 or at least 15 cycles or at least 20 cycles or at least 25 cycles of denaturation, annealing, and ligation can be conducted in an LCR protocol. Thus, LCR can involve contacting a DNA ligase with three or more polynucleotides to form a mixture, annealing the polynucleotides so that a first and second polynucleotide abut one another while annealed to a third (complementary) polynucleotide having a sequence complementary to one or both of the first and second polynucleotides, and performing a ligation between the first and second polynucleotides to result in a nucleic acid product. The polynucleotides are then optionally subjected to denaturing and annealing and the process can be optionally repeated.

LCR can be followed by DNA assembly and/or amplification procedures that utilize a thermostable DNA polymerase (e.g. Taq polymerase) to assemble or amplify the oligos resulting from a successful ligation, for example PCA, OSOS, OE-PCR, or PCR protocols (or combinations and variations of any of them). In different embodiments LCR can be performed with or without primers. In the present invention LCR, PCA, OSOS, or OE-PCR can be performed on short oligos of any size described herein, for example (but not limited to) oligos of less than 30 nucleotides, or less than 22 nucleotides, or less than 20 nucleotides, or less than 15 nucleotides, or less than 12 nucleotides, or short oligos of greater than 6 nucleotides, or greater than 12 nucleotides, or greater than 13 nucleotides, or oligos of 19 nucleotides or 18 nucleotides or 16 nucleotides or less than 16 nucleotides or 8-18 nucleotides or 8-17 nucleotides, or 8-16 nucleotides or 8-15 nucleotides in length. In some embodiments any of these reactions can also include longer, complementary sequences, which in some embodiments can be 2-4 times as long as the short oligos in the mixture. But any of the oligo lengths described herein can be utilized in the LCR or other DNA assembly and/or amplification reactions. In some embodiments the annealing and/or ligation can be performed at or near the melting temperature of one or both of the oligos involved in the ligation reaction, e.g. within 1° C. or 2° C. or 3° C. or 5° C. In various embodiments the LCR can be conducted with at least 2 or at least 3 or at least 8 oligos or at least 16 oligos or at least 32 oligos or at least 64 oligos, or 8-32 oligos or 8-64 oligos, and the oligos can be of any length set forth herein. LCR can include (or be preceded by) phosphorylation of the 5'-P of donor oligonucleotides so that the ligase can join the 5'-P of the donor with the 3'-OH of the acceptor oligo. In one embodiment phosphorylation is performed by contacting the oligos with a kinase, e.g. any described herein. In some embodiments the method is conducted isothermally, i.e. temperature is not varied in a gradient that determines the order of assembly of oligonucleotides. In some embodiments the LCR can be conducted isothermally. In various embodiments any of LCR, PCA, OSOS, and PCR can be carried out without the use of an exonuclease.

To briefly describe the LCR reaction, thermal separation or denaturation of oligos in a set occurs. The temperature is then lowered and the oligos anneal to their complementary strand in the oligo set. The oligos are designed such that two oligos to be joined will anneal directly adjacent to and abut each other on the same complementary strand having complementary sequences for each oligo. The first oligo has a phosphate group on its 5' terminal nucleotide, and the second oligo has a 3' hydroxyl on its 3' terminal nucleotide, thus providing the 5'-P and 3'-OH substrates for the ligase. The ligase then covalently joins the abutting oligos into one (now larger) polynucleotide bound to the complementary strand. In a subsequent cycle the joined polynucleotides are then thermally separated and re-annealed to a complementary strand again, again next to and abutting a directly adjacent oligo, and are again joined by the ligase. One or more further cycles of denaturation, annealing, and ligation can then be performed. A step of phosphorylation of the 5' nucleotides can, optionally, be included. In various embodiments at least 10, or at least 15, or at least 19, or at least 20 cycles, or at least 25 cycles, can be included in an LCR protocol. LCR normally produces a duplex DNA. An example of the LCR protocol is provided in Example 1.

OSOS "one step-one shot" is a PCR-type reaction for assembling DNA using a DNA polymerase, dNTPs, and (optionally) a crowding agent and can (optionally) include amplifying overlapping oligonucleotides to form a nucleic acid product. Details about these reactions can be found, for example, in US 2014/0308710, published Oct. 16, 2014, which is hereby incorporated by reference in its entirety, including all tables, figures, and claims. In one example an OSOS protocol is shown in Example 1. However, persons of ordinary skill with resort to this disclosure will realize the protocol can be varied and adapted depending on the specific nucleic acids being assembled. While in this protocol the reaction is cycled 9 times, in other embodiments it can be cycled at least 5 times, or at least 10 times, or at least 12 times, or at least 15 times, or at least 19 times, or at least 20 times or at least 25 times. OSOS involves cycling of an annealing phase, an extension phase, and a denaturation phase. In OSOS any one or more of the phases can be a time varied phase. A time varied phase is a phase that is conducted for a period of time that varies or changes between cycles. A time varied phase (e.g., a time varied extension phase as shown in step 5 of the protocol) of a cycle can be increased or decreased in time relative to the same phase of the prior cycle or relative to the first such phase of the cycle or relative to the phase of the first cycle of the method. For example, in one embodiment the extension phase of each cycle is a time varied phase. The change in time can be an increase of about 10 seconds/cycle or about 12 seconds per cycle or about 14 seconds per cycle, or about 15 seconds/cycle, or about 17 seconds/cycle or about 20 seconds/cycle. In some embodiments OSOS is performed with primers in the reaction, and in other embodiments OSOS is performed without primers, and the primers can optionally be terminal primers. Primers or terminal primers can be used, e.g. if amplification is also desirable. In various embodiments primers can be at least 3, or at least 4, or at least 5, or at least 6, or 4-6 or 4-8 or 6-15 nucleotides in length. In any embodiment the crowding agent can be polyethylene glycol (e.g. PEG 8000), which can be provided at a concentration of greater than 0.0188% or greater than 0.025% or greater than 0.375% in the reaction buffer.

Thus in one embodiment an OSOS reaction can involve assembling a nucleic acid molecule in a single step from a set of overlapping oligonucleotides. The reaction can involve one or more steps of combining a set of at least five overlapping oligonucleotides with a DNA polymerase, a mixture of dNTPs, and (optionally a crowding agent) in a reaction vessel to form an assembly mixture, subjecting the assembly mixture to at least 25 cycles, each cycle comprising an annealing phase performed at between 50° C. and 77° C., an extension phase performed at between 50° C. and 77° C., and a denaturation phase performed at greater than 90° C., and thereby assembling the nucleic acid molecule from a set of overlapping oligonucleotides in a single step.

Polymerase cycling assembly (PCA) is known to persons of ordinary skill in the art and is a method for the assembly of larger nucleic acid molecules from shorter fragments. PCA can be conducted with the products of the LCR reaction. Similar to how there is a forward primer and a reverse primer capable of allowing DNA polymerase to fill the entire template sequence, PCA uses similar technology but with multiple oligonucleotides. PCA takes advantage of DNA hybridization and annealing and uses DNA polymerase to assemble a sequence of DNA in a precise order based on single-stranded oligos (or overhangs) having complementary sequences. PCA can assemble oligonucleotides or DNA fragments (optionally of at least 30 nucleotides or at least 60 nucleotides) into a larger DNA molecule. Using a cycling reaction involving phases of annealing, extension, and denaturation larger DNA molecules can be assembled. In any embodiment the PCA reaction can be conducted without primers (e.g. terminal primers). But in some embodiments such primers can be used in a PCA protocol, e.g. if amplification is desirable.

In some embodiments the DNA ligase used in LCR is a thermostable ligase. For example, when a thermostable DNA ligase is used it can be Taq ligase. But other ligases can also be used, e.g. Pfu DNA ligase, or others. In one embodiment the thermostable ligase can maintain its activity at a temperature of greater than 45° C. for at least one hour. In some embodiments the thermostable ligase used in the methods is active at about 45-65° C. or from 45-80° C., optionally for at least one hour. In some embodiments the ligase has a half-life of at least 48 hat 65° C. and/or a half-life of greater than I hour at 95° C. In some embodiments the activity of the ligase is NAD-dependent, and in such cases NAD is present in the reaction mixture. By "active" is meant at least 50% of the activity of a reaction conducted under standard reaction conditions to evaluate the enzyme.

In some embodiments the plurality or set of oligos to be joined in the methods (or in the LCR, PCA, OSOS, OE-PCR reactions that can be used in the methods) are present in solution, i.e. in some embodiments none of the oligos in the plurality or set are immobilized on or bound to a microarray, DNA chip, bead, or other solid support that binds one or more of the oligos, nor is any reaction component so immobilized or bound. In one embodiment all of the short oligos to be assembled into a longer oligo or DNA fragment or DNA molecule of desired sequence are present in solution. Since the methods can be applied using oligonucleotides in solution they are therefore amenable to automation.

The longer oligos or DNA fragments produced by the ligase chain reaction can be further assembled by any DNA assembly technique, e.g. OSOS and/or polymerase cycling assembly (PCA). In various embodiments the LCR reactions or the methods disclosed herein can be conducted as a single step or one-step reaction, meaning that once reaction components are placed into the reaction vessel the reaction is conducted and the DNA molecule of desired sequence assembled without needing to re-open the vessel and, optionally, the vessel does not have to be opened during subsequent DNA assembly reactions (e.g. PCA and/or PCR reactions) either, when used. In any embodiment LCR can be followed by an DNA assembly reaction (e.g. OSOS). LCR can also be followed by a PCA reaction. LCR can also be followed by a PCA reaction, and optionally a DNA assembly reaction. In any of the embodiments the series of reactions can be followed by PCR for amplification. When PCA and/or PCR are used, the short oligonucleotides and DNA ligase can form a mixture, and after performing LCR the resulting longer oligos or DNA fragments can be contacted with a DNA polymerase and dNTPs and any other necessary component to join the set of longer oligos or DNA fragments, and to thereby assemble the DNA molecule having the desired sequence.

Exemplary Embodiments

In one embodiment a DNA molecule of desired sequence is assembled in the method where the mixture of DNA ligase and short oligonucleotides contains from 2-250 short oligos of 8-30 or 8-22 nucleotides in length. LCR is followed by PCA and PCR in one embodiment. In other embodiments the DNA molecule of desired sequence is assembled from 8-150 short oligos of 8-30 or 8-22 nucleotides in length. The short oligos can optionally comprise at least 50% or at least 75% or at least 90% of the polynucleotides present in the mixture (by molar ratio or w/w). In this embodiment the method can be performed entirely in solution. Optionally, there can be present in the mixture no oligonucleotides longer than 30 nucleotides in length, but also optionally there can be present longer oligonucleotides where less than 10% or less than 5% or less than 3% or less than 1% (by molar ratio) of the oligonucleotides in the mixture have a length of longer than 30 nt. In a particular embodiment the short oligonucleotides are 8-mers or 16-mers or have a length of 8-16 nucleotides. In any embodiment herein the assembled DNA molecule can have an error rate of less than 1 error per 10,000 nucleotides. In any of the embodiments the DNA molecule of desired sequence can have a GC content of at least 30% or 30-60%.

In one embodiment the methods involve contacting DNA ligase with a plurality of short oligos of 8-22 nucleotides in length to form a mixture. At least 50% of the short oligos can be 8-22 nucleotides in length or 10-22 nucleotides in length; or, optionally, at least 70% or at least 90% or 100% of the short oligos in the DNA ligase mixture can be 8-22 or 10-22 nucleotides in length. In a particular embodiment the short oligos are 8-mers or 16-mers or 8-16 nucleotides in length. In this embodiment the method can be performed entirely in solution. Optionally, no oligonucleotides longer than 22 nucleotides in length are present in the mixture, but also optionally there can be present longer oligonucleotides in a small quantity of longer polynucleotides, e.g. less than 10% or less than 5% or less than 3% or less than 1% (by number of oligos) of the oligonucleotides in the mixture have a length of longer than 20 nt or 22 nt. In a particular embodiment the short oligonucleotides are 8-mers or 16-mers or have a length of 8-16 nucleotides. In any embodiment herein the assembled DNA molecule can have an error rate of less than 1 error per 8,000 or 10,000 nucleotides.

In another embodiment the methods involve contacting DNA ligase with a plurality of short oligos of 14-20 nucleotides in length to form a mixture or 16-18 nucleotides in length. At least 50% or at least 75% or at least 90% of the short oligos can be 16-18 nucleotides in length, or from 15-19 nucleotides in length, or from 14-20 nucleotides in length. In a particular embodiment the short oligos are 16-mers or 17mers or 18-mers. In this embodiment the method can be performed entirely in solution. Optionally, no oligonucleotides longer than 20 nucleotides in length are present in the mixture, but also optionally there can be present longer oligonucleotides in a small quantity of longer polynucleotides, e.g. less than 10% or less than 5% or less than 3% or less than 1% (by number of oligos) of the oligonucleotides in the mixture have a length of longer than 20 nt. In any embodiment herein the assembled DNA molecule can have an error rate of less than 1 error per 8,000 or 9,000 or 10,000 nucleotides.

In any embodiment the DNA molecule of desired sequence can be assembled in the method from overlapping sets of 14×8mers. Various numbers of sets can be used, for example five or seven or nine.

In one embodiment a DNA molecule of desired sequence is assembled in the method from a mixture containing 6 pools of 32 oligos, or 2 pools of 64 oligos, or 1 pool of 111 oligos. LCR is optionally followed by OSOS and/or PCA and/or PCR.

In one embodiment a DNA molecule of desired sequence is assembled in the method from a mixture containing more than 65 short oligonucleotides.

In any embodiment of the methods the mixture can contain short oligonucleotides that overlap by about one-half the length of the short oligo, e.g. within 1-2 nucleotides of the length. For example in any embodiment of the methods the mixture can contain short oligonucleotides that are 8mers and overlap by 4 nt, or are 16mers and overlap by 8 nt, or 8mers that overlap by 3-5 nt or 16mers that overlap by 7-9 nt.

In any embodiment of the methods LCR is conducted with 64 oligos, or with more than 65 oligos, or with more than 65 oligos.

In any embodiment LCR can be followed by a DNA assembly reaction (e.g. OSOS) having a time varied phase, where the time varied phase is the extension phase and the extension phase is increased by 15 second/cycle.

Example 1

Figure 2:
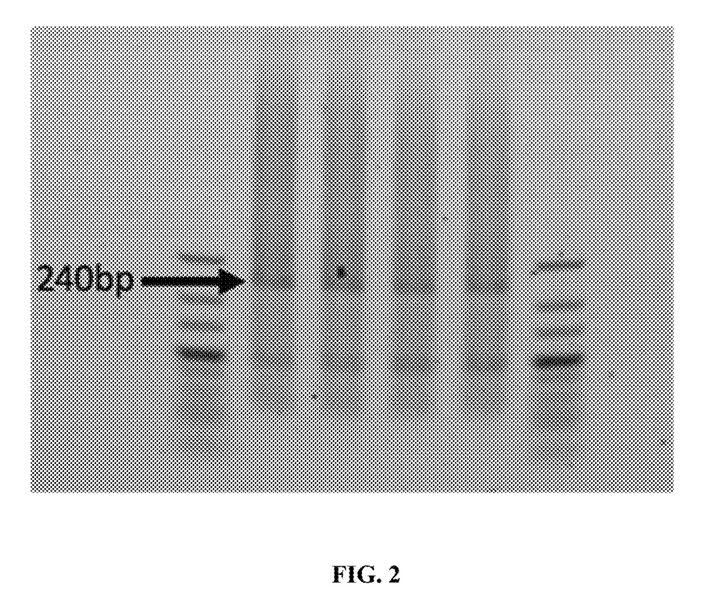
FIG. 2 is an illustration of an agarose gel showing the formation of a 240 bp product. Shown is the result of assembling the 240 bp product from seven overlapping sets of 14×8-mers.

This example shows the synthesis of a 240 bp DNA fragment of a randomly generated synthetic sequence having about 50% GC content. Seven overlapping pools of 14 8-mers (14×8mer) containing oligos having a 4 bp overlap were ligated using T4 DNA ligase to form seven pools of 60-mers, where the pools overlap with oligos in an adjacent pool. After LCR these seven pools of 60mers were then placed into one pool and the final 240 bp product assembled by the polymerase chain assembly reaction. The 240 bp product is indicated in FIG. 2. The cloning and Sanger sequencing of 96 clones for the final 240 bp product was performed for verification (Table 1) using the Zero Blunt® PCR Cloning Kit for cloning of blunt end PCR products (ThermoFisher, Waltham, MA).

Two pools were formed at 25 nl volume using an acoustic liquid handling system to dispense fluids, with water added to 16 ul for a concentration of about 30 nM/oligo. To each 16 ul pool was added 10 ul of master mix containing a 1:1 ratio of T4PNK mixture and LCR mixture and mixed well and incubated in a thermocycler according to the below protocol for about 5 hours for phosphorylation, denaturing and annealing, and LCR. T4PNK mixture contained 2 ul water, 2 ul 10×T4 DNA ligase buffer, and 1 ul T4PNK. LCR mix had 1.5 ul water, 2.5 ul 10× Taq ligase buffer, and 1 ul Taq ligase. The T4PNK-LCR protocol was as follows:

1. 37° C. 30 min
2. 98° C. 2 min
3. 85° C. 2 min, ramp 1° C./s
4. 50° C. 5 min, ramp 0.1° C./s
5. 37° C. 5 min
6. 95° C. 10 sec
7. 85° C. 1 min, ramp 1° C./s
8. 55° C. 1 min, ramp 1° C./s
9. 50° C. 2 min
10. 45° C. 5 min
11. Go to 6, 9×
12. 95° C. 10 sec
13. 65° C. 5 min
14. 55° C. 10 min
15. 50° C. 5 min
16. 45° C. 5 min
17. Go to 12, 19×
18. 50° C. 30 min
19. 10° C. 0 (forever)

After the PNK-LCR protocol 20 ul of PCA mix (PCR mix with Phusion® DNA polymerase (Finnzymes Oy, Vantaa, Finland) with 50 mM TMAC (tetramethyl ammonium chloride) and no primers) was added to each of the wells with 6 ul of master mix, as above. Ten cycles of OSOS "one step one shot" (a PCR-type protocol) were performed using the following protocol:

1. 98° C. 1 min
2. 98° C. 30 sec
3. 68° C. 1 min
4. 60° C. 1 min
5. 55° C. 1 min, add 15 sec/cycle
6. 50° C. 1 min
7. Go to 2, 9×
8. 72° C. 5 min
9. 10° C. 0 (forever)

20 ul of PCR mix (with primers) were added to each of the wells with a PCA reaction. PCR was performed using the following protocol:

1. 98° C. 1 min
2. 98° C. 30 sec
3. 72° C. 45 sec, add 15 sec/cycle
4. 55° C. 1 min, add 15 sec/cycle
5. Go to 2, 9×
6. 98° C. 30 sec
7. 72° C. 4 min
8. 65° C. 6 min
9. Go to 6, 19×
10. 72° C. 5 min
11. 10° C. 0 (forever)

Products were then loaded onto gels for confirmation of formation of the desired DNA molecule, shown in FIG. 2.

TABLE 1

| | |
|---|---|
| Total Reads | 95 |
| FL Reads (240 bp) | 60 |
| Partial reads (missed 3) (183 bp) | 27 |
| Partial reads (missed 5') (various) | 8 |
| Error on FL | 1 (snp C->A) |
| ER | 14400 |

As shown in Table 1, cloning and sequencing confirmation of the final assembly revealed an overall error rate of 1 in 14,400 bp. This is approximately 14 times higher sequence fidelity than what is obtained in synthetic DNA constructs using standard 40-mers (without exposure to an enzymatic step of error-correction). This resulted in a percent error-free molecule (% EFM) rate of about 95%, where the % EFM describes the percent of colonies per clone that are expected to be error-free if sequenced in their entirety.

Example 2

Figure 3:
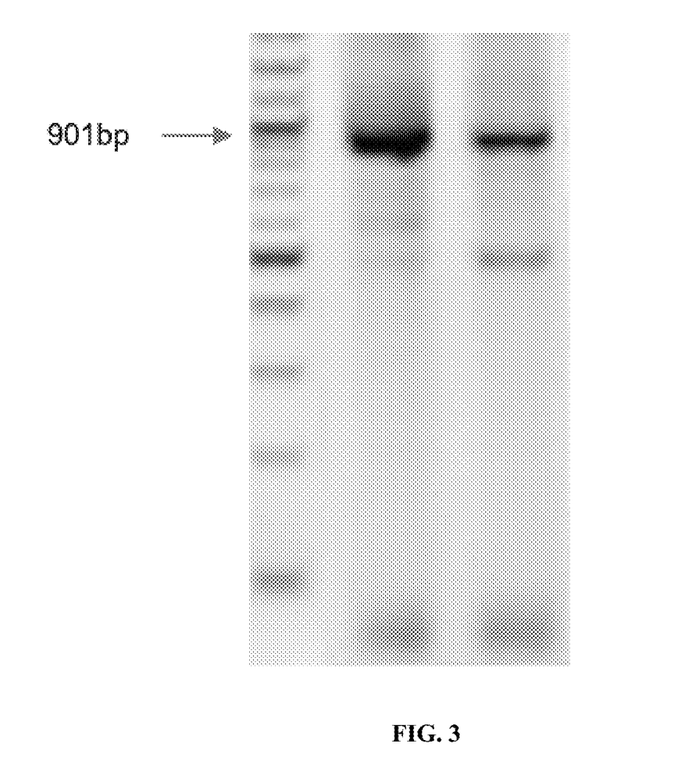
FIG. 3 is an illustration of an agarose gel illustrating the result of assembling GFP from 16mer pools into a 901 bp GFP sequence. Lane 1 shows synthesis from six pools of 32×16mers, then all placed into one pool for PCA and PCR. Lane 2 shows synthesis from 2 sub-pools of 64×16mers, and then placing into one pool for LCR. LCR was followed by PCA and PCR (LCR->PCA->PCR).

This example shows the synthesis of GFP fragments from 16-mers, 30-mers and 40-mers. Protocols used are the same as provided in Example 1. First, pools of short oligonucleotides (16-mers) were used to construct the 901 bp sequence of GFP. Varying numbers of 16mers were used in various dilutions with Taq ligase. The pool sizes were 6 pools of 32×16mers, 2 pools of 64×16mers and a single pool of 111 16mers. Oligos were 5' phosphorylated using T4 polynucleotide kinase and assembled using the ligase chain reaction, which was followed by PCA and PCR to assemble and amplify the DNA product. Successful assemblies were achieved for all pool sizes, as shown in FIG. 3a. Gels were done and confirmation of assembly is provided in FIG. 3a.

Sequencing was performed for confirmation of the sequence of the resulting DNA molecule. An error rate of 1 error per 8500 bp was observed for a subset of the assembled DNA molecules. It was therefore demonstrated that a highly complex mixture of short oligos can be assembled using the method involving LCR and PCA/PCR. For comparison 30mers and 40mers were synthesized and used in the method to assemble and amplify GFP assembled from single pools of 30mers and 40mers for LCR. LCR was followed by OSOS and PCR. The method also successfully assembled all pool sizes, demonstrating robustness of the methods. [Resulting gels are depicted in FIG. 3b.]

Example 3

Figure 4A:
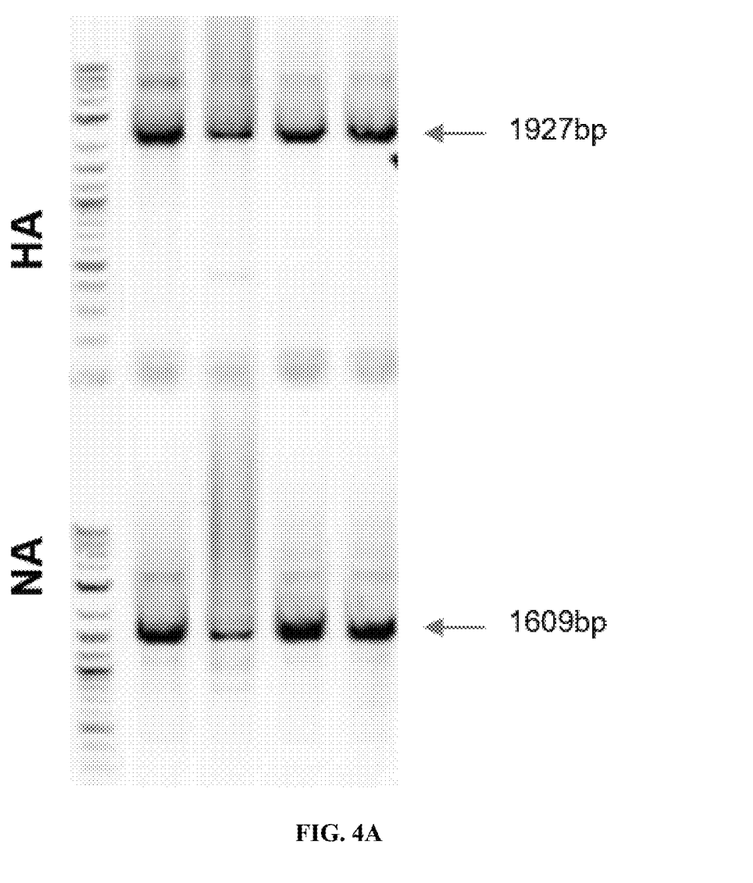
FIG. 4A is an illustration of agarose gels illustrating the result of assembling 1927 bp and 1609 bp HA and NA (respectively) from 30mer and 40mer pools. Lane 1: assembly with LCR with sub-pools of 16mers, with each sub-pool containing 64 of 16mer oligos overlapping (128 bp) with adjacent sub-pools. Lane 2 shows LCR with all 16mers. Lane 3: LCR with all 30mers. Lane 4: LCR with all 40mers. Protocols were as shown in Example 1.

To demonstrate that the method can assemble larger DNA molecules the influenza HA (1927 bp) and NA (1609 bp) nucleic acids having vector ends were assembled using the method. Various pooling scenarios were performed and successfully assembled the DNA molecule, including 16mers split into five sub-pools (each sub-pool containing 64 oligos overlapping (128 bp) with adjacent sub-pools), 16mers as a single pool, 30mers as single pools, and 40mers as single pools. Sequencing confirmation of the assembled nucleic acid molecules showed that 92% and 89% of the HA and NA were assembled as error free molecules. This compared to assembly of the molecules from 60mers, where 37% and 29% of the HA and NA molecules were assembled as error free molecules. Resulting gel is depicted in FIG. 4a.

Example 4

Figure 4B:
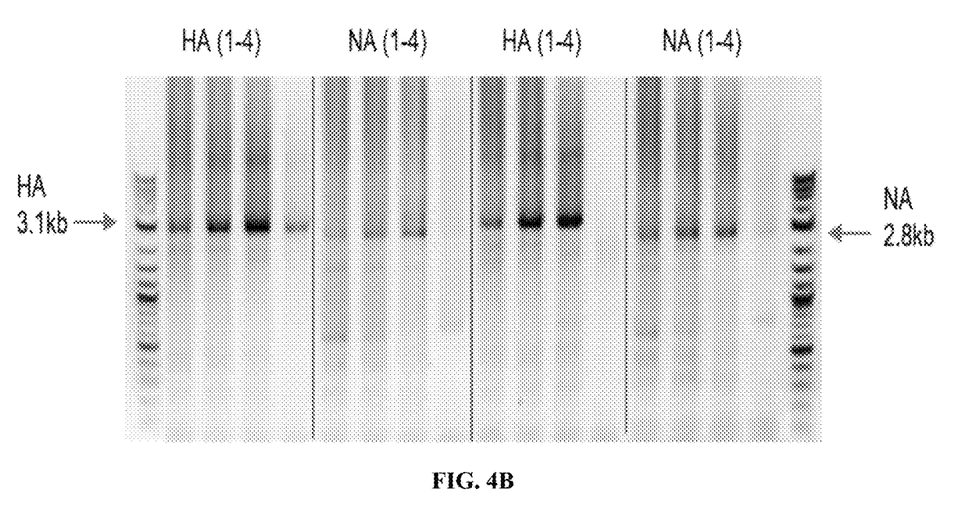
FIG. 4B is an illustration of an agarose gel showing dilutions of assembly of HA and NA from pools of eight 16mers and four 16mers using LCR followed by PCA and PCR. Dilutions 1-4 for LCR are 2.5×, 5×, 10×, and 20×.

This example shows the assembly of 3100 bp HA and 2800 bp NA nucleic acid constructs using 16mers under various pooling scenarios including 8×16mer oligos and 4×16mer, which were found to successfully assemble the desired DNA molecule of specific sequence using the disclosed method including LCR and followed by a step of polymerase cycling assembly (PCA), which was followed by another step of PCR, all performed according to the protocols in Example 1. Results are illustrated in FIG. 4b.

Example 5

Figure 5:
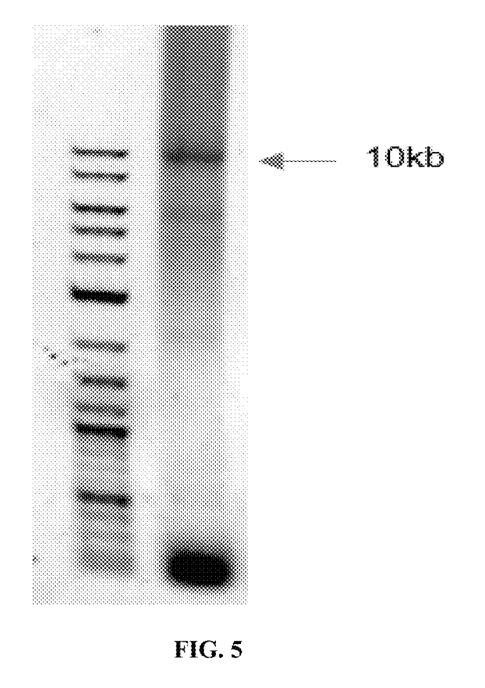
FIG. 5 shows a gel demonstrating assembly of a 10 kb DNA product assembled from 26 overlapping pools of 16mers by LCR followed by PCA and PCR amplification.

This example shows assembly of a 10 kb portion of the *Bacillus subtilis* genome sequence using 26 overlapping pools of 16mers using LCR followed by PCA and PCR for the final assembly using protocols as shown in Example 1. FIG. 5 demonstrates formation of the 10 kb product.

Example 6

Figure 6:
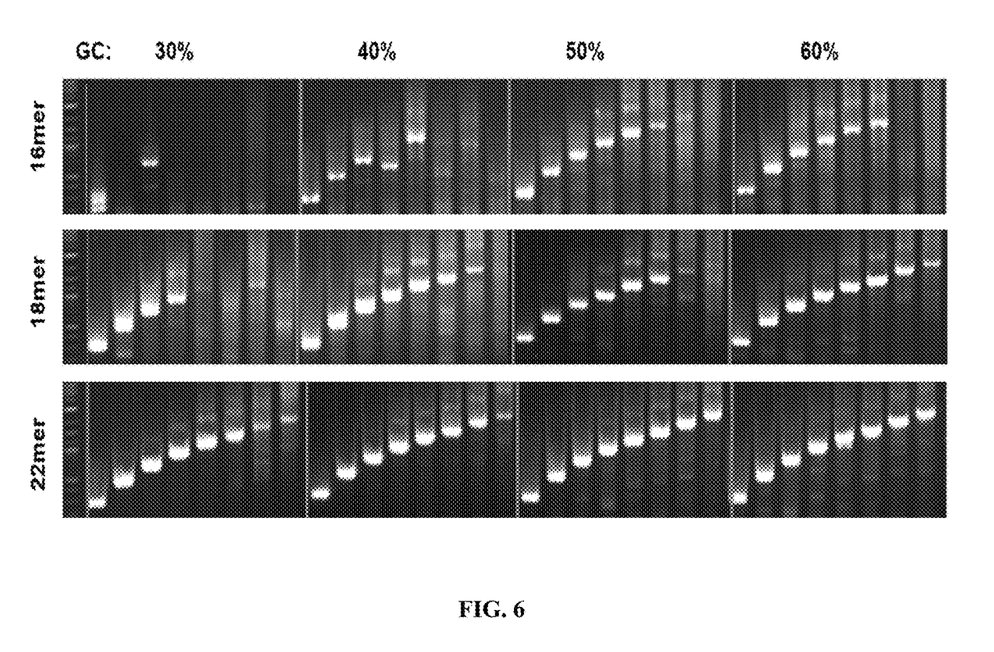
FIG. 6 is an illustration of agarose gels illustrating the results of assembling 32 constructs of variable GC content from 16mers, 18mers, or 22mers, each assembled in 1 pool. Columns 1-8 of each gel show the size of the construct assembled according to columns 1-8 on each gel: 1. 200 bp; 2. 400 bp; 3. 600 bp; 4. 800 bp; 5. 1000 bp; 6. 1200 bp; 7. 1500 bp; 8. 1800 bp. Oligos were subjected to LCR-PCA-PCR according to Example 1 protocols.
Figure 7:
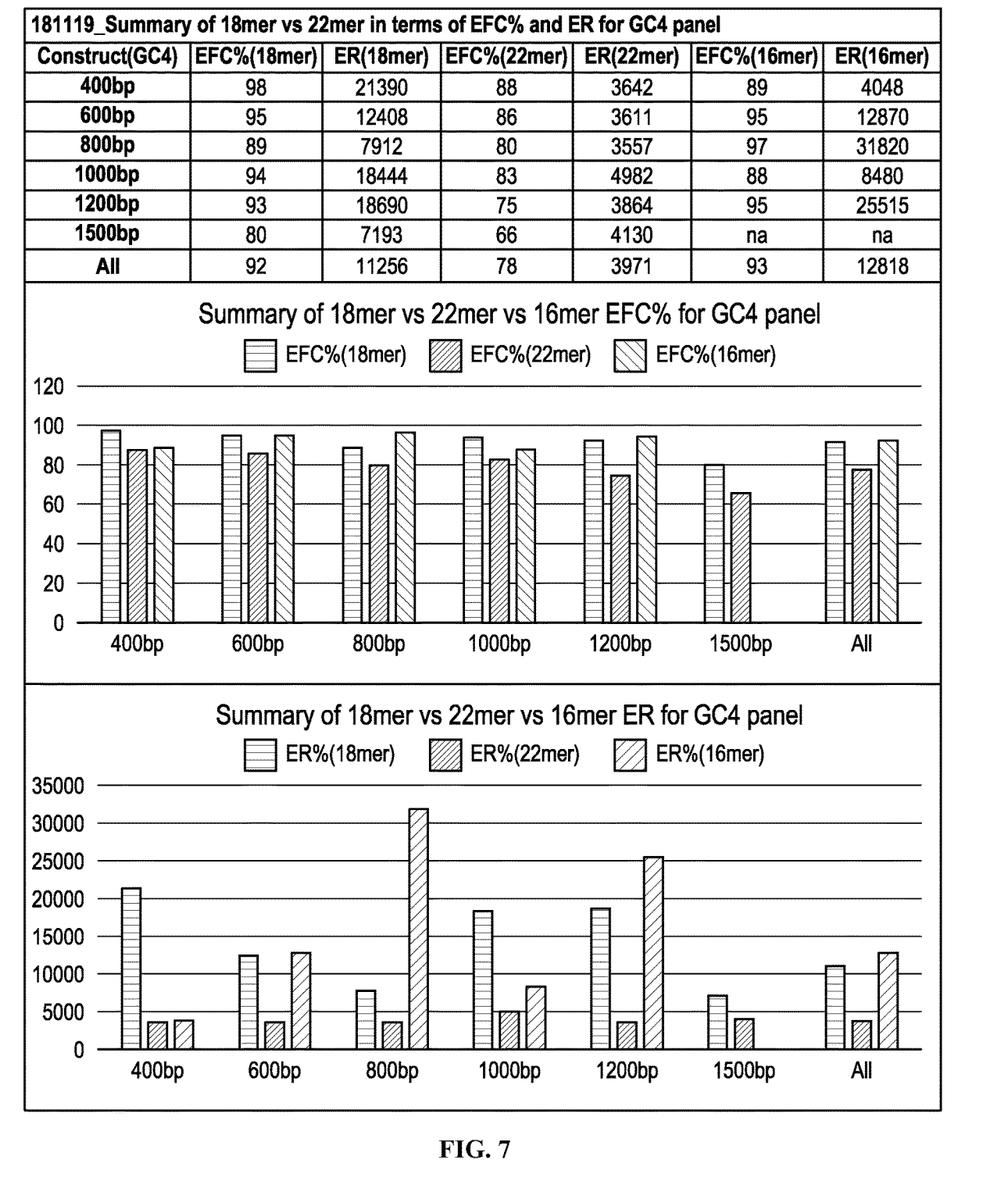
FIG. 7 is a table and graphical illustrations of a table and two bar graphs showing the error rate and percent error free constructs assembled for 16mers, 18mers, and 22mers. ER signifies error rate, % EFC signifies the percent of error free constructs obtained. An overall error rate of 1 in 11,000 base pairs was achieved with 16mers and the percent of error free constructs varied from 88-97%.

This example demonstrates that the present method achieves significantly higher sequence fidelity than other methods. Thirty-two DNA constructs ranging in size from 200 bp to 1800 bp and having varying degrees of GC content were assembled from 16mers, 18mers, and 22mers. The GC percentages were 30%, 40%, 50% or 60% (GC4 panel). Gels are depicted in FIG. 6. As shown in FIG. 6, assembly was robust and successfully performed with all small oligo sizes and at all levels of GC content. FIG. 7 illustrates that the highest sequence fidelity was obtained starting with 16mers and 18mers.

What is claimed is:

1. A method of assembling a DNA molecule having a desired sequence comprising:
   a) contacting a DNA ligase with short oligonucleotides of 8-25 nucleotides in length and comprising at least a portion of the desired sequence of the DNA molecule to be assembled to create a mixture,
   wherein at least a portion of the short oligonucleotides in the mixture overlap with and are complementary to a portion of the sequence of at least one other short oligonucleotide in the mixture, and wherein at least two of the short oligos abut one another when bound to their complementary sequence(s),
   b) performing a ligase chain reaction on the mixture to thereby generate a set of polynucleotides, and
   c) contacting the set of polynucleotides with a DNA polymerase and dNTPs to join the set of polynucleotides, and to thereby assemble the DNA molecule having the desired sequence
   wherein the method is performed as a one-step reaction.

2. The method of claim 1, wherein the set of polynucleotides is joined by a DNA assembly reaction.

3. The method of claim 2, further comprising combining multiple pools of the set of DNA fragments to join the DNA fragments via PCA (Polymerase Cycling Assembly).

4. The method of claim 1, wherein the set of polynucleotides is joined by polymerase cycling assembly.

5. The method of claim 1, further comprising contacting the short oligonucleotides with a kinase before or simultaneous with the contacting of the short oligonucleotides with the DNA ligase.

6. The method of claim 1, wherein the DNA ligase is a thermostable DNA ligase.

7. The method of claim 6, wherein the DNA ligase is Taq ligase.

8. The method of claim 1, wherein the abutting short oligos comprise a phosphorylated 5' terminal nucleotide of a first short oligo and a 3' hydroxyl on a 3' terminal nucleotide of a second short oligo.

9. The method of claim 1, further comprising amplifying the DNA molecule having the desired sequence using the polymerase chain reaction.

10. The method of claim 1, wherein the method is performed in solution.

11. The method of claim 1, wherein the DNA molecule having the desired sequence is 100-10,000 base pairs in length.

12. The method of claim 1, wherein the DNA molecule having the desired sequence is 100-5,000 base pairs in length.

13. The method of claim 1, wherein the desired sequence further comprises a universal 5' flanking sequence and a universal 3' flanking sequence.

14. The method of claim 1, wherein the mixture comprises at least 10 short oligonucleotides.

15. The method of claim 14, wherein the mixture comprises at least 20 short oligonucleotides.

16. The method of claim 1, wherein the mixture comprises from 2 to 250 short oligonucleotides.

17. The method of claim 1, wherein the short oligonucleotides are 8-18 nucleotides in length.

18. The method of claim 1, wherein at least 50% of the short oligonucleotides in the mixture are 16-18 nucleotides in length.

19. The method of claim 1, wherein at least 75% of the oligonucleotides in the mixture are 8-18 nucleotides in length at the start of the method.

20. The method of claim 1, wherein the method is performed without the use of restriction enzymes.

21. The method of claim 1, wherein assembled DNA molecule of desired sequence has an error rate of fewer than 1 error per 2000 base pairs.

22. The method of claim 21, wherein the assembled DNA molecule of desired sequence has an error rate of fewer than 1 error per 14000 base pairs.

23. The method of claim 22, wherein the error rate is obtained in the method without the use of error correction enzymes.

24. The method of claim 1, wherein the mixture of short oligonucleotides comprises at least 15 pools of oligonucleotides.

25. The method of claim 1, wherein the assembly is done entirely in vitro.

26. The method of claim 1, wherein the oligonucleotides are 8-mers or 16mers.

27. The method of claim 1, wherein the DNA molecule is assembled with scarless assembly.

28. The method of claim 1, wherein the short oligonucleotides comprise more than 64 short oligonucleotides.

29. The method of claim 1, wherein the method is conducted without the use of linker, adaptor, or spacer DNA molecules.

30. The method of claim 1, wherein the ligase chain reaction comprises at least 5 cycles of denaturation, annealing, and ligation.

31. The method of claim 1, wherein less than 10% of the oligonucleotides in the mixture are longer than 21 nucleotides in length.

32. The method of claim 1, wherein less than 1% of the oligonucleotides in the mixture are longer than 21 nucleotides in length.

* * * * *